United States Patent
Koch et al.

(10) Patent No.: US 8,728,505 B2
(45) Date of Patent: May 20, 2014

(54) SYNERGISTICALLY ACTIVE MIXTURES OF α,ω-AMINO ALCOHOL ENANTIOMERS, PREPARATION THEREOF AND USE THEREOF IN INSECT- AND MITE-REPELLENT FORMULATIONS

(75) Inventors: Burkhard Koch, Köln (DE); Andreas Job, Köln (DE); Nikolaus Müller, Wallhausen (DE)

(73) Assignee: Saltigo GmbH, Leverkusen (DE)

( * ) Notice: Subject to any disclaimer, the term of this patent is extended or adjusted under 35 U.S.C. 154(b) by 321 days.

(21) Appl. No.: 13/155,738

(22) Filed: Jun. 8, 2011

(65) Prior Publication Data
US 2012/0083509 A1  Apr. 5, 2012

(30) Foreign Application Priority Data
Jun. 12, 2010  (DE) .................. 10 2010 023 586

(51) Int. Cl.
*A01N 47/16* (2006.01)
*A01P 7/00* (2006.01)

(52) U.S. Cl.
USPC ........................... 424/405; 514/315; 546/245

(58) Field of Classification Search
None
See application file for complete search history.

(56) References Cited

U.S. PATENT DOCUMENTS

| | | | |
|---|---|---|---|
| 4,900,834 A | 2/1990 | Kruger et al. | |
| 5,008,261 A | 4/1991 | Kruger et al. | |
| 2011/0034510 A1 | 2/2011 | Gernot et al. | |

FOREIGN PATENT DOCUMENTS

WO    WO 2008/046889    *  4/2008    ............. A01N 47/18

OTHER PUBLICATIONS

Natarajan R., et al., "Chirality index, molecular overlay and biological activity of diastereoisomeric mosquito repellents" Pest Manag Sci, Bd. 61, 1193-1201 (2005).
Raffa, et al., "Complementary and Synergistic Antinociceptive Interaction between the Enantiomers of Tramadol", The Journal of Pharmacology and Experimental Therapeutics, vol. 267, No. 1 (1993).
European Search Report in co-pending Application No. 11169399, Oct. 25, 2011, 2 pages.
Chang, et al., "Differences in mutagenicity and cytotoxicity of (+)- and (-)-benzo[a]pyrene 4,5-oxide: A synergistic internation of enantiomers", Proc. Natl. Acad Sci. USA, vol. 76, No. 9, pp. 4280-4284 (1979).
Kochhar, et al., "A Critical Analysis of 'Deet' as a Repellent Against Arthropods of Public Health Importance and Water Leeches", Indian J Med Res 62, 1 pp. 125-133 (1974).
Buchel, "Insekten-Repellents", Chemistry of Crop Protectants and Pesticides, p. 487 ff. (1970).

* cited by examiner

*Primary Examiner* — Kortney L Klinkel
(74) *Attorney, Agent, or Firm* — Nicanor A. Kohncke

(57) ABSTRACT

What are described are insect- and mite-repellent compositions comprising at least 2 enantiomers selected from the group of 1-[(S)-sec-butyloxycarbonyl]-2-(S)-(2-hydroxyethyl)piperidine (referred to hereinafter as S,S), 1-[(R)-sec-butyloxycarbonyl]-2-(R)-(+)-(2-hydroxyethyl)piperidine (referred to hereinafter as R,R), 1-[(S)-sec-butoxycarbonyl]-2-(R)-(+)-(2-hydroxyethyl)piperidine (referred to hereinafter as S,R), 1-[(R)-sec-butyloxycarbonyl]-2-(S)-(+)-(2-hydroxyethyl)piperidine (referred to hereinafter as R,S), excluding the racemate mixture thereof, a process for preparation thereof and the use thereof in insect- and mite-repellent formulations.

10 Claims, No Drawings

SYNERGISTICALLY ACTIVE MIXTURES OF α,ω-AMINO ALCOHOL ENANTIOMERS, PREPARATION THEREOF AND USE THEREOF IN INSECT- AND MITE-REPELLENT FORMULATIONS

The present invention relates to synergistically active mixtures of enantiomerically enriched α,ω-amino alcohol derivatives based on at least two enantiomers of the compound 1-sec-butyloxycarbonyl-2-(2-hydroxyethyl)piperidine (also known as 1-methylpropyl 2-(2-hydroxyethyl)piperidine-1-carboxylate; CAS No. 119515-38-7), to the preparation thereof and to the use thereof in insect and mite repellents. 1-sec-Butyloxycarbonyl-2-(2-hydroxyethyl)piperidine has the following structure of the formula (1)

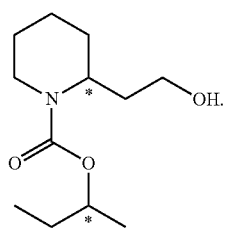

(1)

The racemate of the compound (1) is known by the trade name Saltidin® (other names: Picaridin, Icaridin, formerly Bayrepel®).

Insect or mite repellents have the task of preventing harmful or annoying arthropods from touching, and also from stinging and sucking and biting, on surfaces which attract them, for instance on the skin of animals and humans, when they have been treated with such repellents beforehand.

Numerous active ingredients have already been proposed as repellents (cf., for example K. H. Büchel in Chemie der Pflanzenschutz- und Schädlingsbekämpfungsmittel [Chemistry of crop protection compositions and pesticides]; editor: R. Wegler, vol. 1, Springer Verlag Berlin, Heidelberg, N.Y., 1970, p. 487 ff).

Particularly well-known examples which have been in use for some time are N,N-diethyl-3-methylbenzamide (DEET), dimethyl phthalate and 2-ethylhexane-1,3-diol, among which DEET in particular has gained considerable significance in practice (see, for example, R. K. Kocher, R. S. Dixit, C. I. Somaya; Indian J. Med. Res, 62, 1(1974)).

Additionally known are substituted am-amino alcohol derivatives in the form of the racemic mixture of the individual enantiomers, as obtained in the chemical synthesis (EP-A-289 842). Even in the form of the racemic isomer mixtures used, these possess a strong insect- and mite-repellent action. Saltidin®, which has already been mentioned, has been found to be particularly effective.

A disadvantage of all known repellents is their sometimes relatively short-lived duration of action (only a few hours).

EP-A-2086327 describes the preparation and use of individual enantiomerically enriched α,ω-amino alcohol derivatives as insect and mite repellents. The use of individual enantiomers exhibited a prolonged efficacy in some cases compared to the racemate. However, only individual enantiomers were examined for their efficacy in comparison to the racemic mixture.

The synergistic action of mixtures of individual enantiomers is known from the literature in individual cases in pharmacology and toxicology. For example, Proc Natl Acad Sci 1979, 76 (9), 4280-4 describes the synergistic cytotoxic and mutagenic action of the mixtures of enantiomers of benzo [a]pyrene 4,5-oxide.

One example of complementary action of enantiomers can be found, in contrast, in Pharmacol Exp Ther 1993, 267 (1), 331-40. Some of the enantiomers of the active ingredient tramadol exhibit a distinct reduction in action compared to the racemate (complementary interaction).

However, the synergistic action of enantiomer mixtures as an insect and mite repellent is unknown to date.

It was an object of the present invention to find insect and mite repellents which exhibit a prolonged duration of efficacy compared to the repellents known to date.

It has now been found that, surprisingly, particular mixtures of individual enantiomers of α,ω-amino alcohol derivatives of the formula (1) have a synergistic effect with respect to the duration of action as an insect and mite repellent compared to the racemate mixture. The extension of the duration of action compared to the racemic mixture is much higher than expected by virtue of simple addition of the duration of action of the individual enantiomers.

The present invention therefore provides insect- and mite-repellent compositions comprising at least 2 enantiomers selected from the group of 1-[(S)-sec-butyloxycarbonyl]-2-(S)-(2-hydroxyethyl)piperidine (referred to hereinafter as S,S), 1-[(R)-sec-butyloxycarbonyl]-2-(R)-(+)-(2-hydroxyethyl)piperidine (referred to hereinafter as R,R), 1-[(S)-sec-butoxycarbonyl]-2-(R)-(+)-(2-hydroxyethyl)piperidine (referred to hereinafter as S,R), 1-[(R)-sec-butyloxycarbonyl]-2-(S)-(+)-(2-hydroxyethyl)piperidine (referred to hereinafter as R,S), excluding the racemate mixture thereof.

1-sec-Butyloxycarbonyl-2-(2-hydroxyethyl)piperidine has 2 optically active carbon atoms, which are indicated by (*) in formula (1)

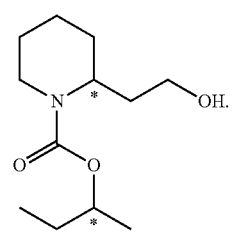

(1)

Accordingly, this compound has 4 enantiomers with the designations given above. The individual enantiomers are referred to hereinafter, with regard to their configurations, by the abbreviations S,S; R,R; S,R and R,S.

In addition to an increase in efficacy compared to the racemate mixture which comprises all 4 enantiomers in a weight ratio of (1:1:1:1), the inventive compositions avoid use of inactive or less active enantiomers, which may be advantageous with regard to tolerance in humans.

Preferably, the inventive composition comprises 2 or 3 enantiomers, in which case the particular enantiomers may be present in the 2- or 3-component mixtures in a wide variety of different weight ratios relative to one another.

In the case of the inventive 2-component mixtures, preference is given to those which each comprise the S,S/R,S; S,R/R,S; R,S/R,R; S,S/S,R or S,R/R,R enantiomers in a weight ratio of 1:1. Particular preference is given to the 2-component mixtures which comprise the R,S/R,R; S,S/S,R or S,R/R,R enantiomers. Compared to the racemate mixture, these inventive compositions exhibit a duration of action increased by 21%, 15% and 18% respectively.

In the case of the inventive 3-component mixtures, preference is given to those which each comprise the R,R/R,S/S,R; S,S/R,S/S,R; S,S/S,R/R,R or S,S/R,R/R,S enantiomers in a weight ratio of 1:1:1. Particular preference is given to the 3-component mixtures which comprise the enantiomers S,S/S,R/R,R; S,S/R,R/R,S or S,S/R,S/S,R. Compared to the racemate mixture, these inventive compositions exhibit a duration of action increased by 28%, 25% and 13% respectively.

The individual enantiomers are obtained by reacting optically active α,ω-amino alcohols (e.g. (S)- or (R)-2-(2-hydroxyethyl)piperidine) with chlorocarbonic esters which are known per se and contain an optically active (R)- or (S)-sec-butyl radical, as described, for example, in EP-A-2086327.

Alternatively, the individual enantiomers can also be isolated from the racemate mixture by methods known per se, for example by chromatography on suitable optically active carriers. The inventive compositions are then prepared by blending the individual enantiomers in the desired weight ratio.

The invention further provides a process for preparing insect- and mite-repellent compositions which comprise 2 or 3 enantiomers selected from the group of 1-[(S)-sec-butyloxycarbonyl]-2-(S)-(2-hydroxyethyl)piperidine, 1-[(R)-sec-butyloxycarbonyl]2-(R)-(+)-(2-hydroxyethyl)piperidine, 1-[(S)-sec-butoxycarbonyl]-2-(R)-(+)-(2-hydroxyethyl)piperidine and 1-[(R)-sec-butyloxycarbonyl]-2-(S)-(+)-(2-hydroxyethyl)piperidine, in which 2 enantiomers for the 2-component mixture, and 3 enantiomers for the 3-component mixture, are mixed with one another, optionally in a solvent, for example water. Preference is given to performing the process according to the invention for preparing insect- and mite-repellent compositions in such a way that 2 enantiomers for the 2-component mixture, for example the S,S/R,S; S,R/R,S; R,S/R,R; S,S/S,R or S,R/R,R enantiomers, are mixed with one another in a ratio of 1:1, and 3 enantiomers for the 3-component mixture, for example the R,R/R,S/S,R; S,S/R,S/S,R; S,S/S,R/R,R or S,S/R,R/R,S enantiomers, are mixed with one another in a ratio of 1:1:1. Particular preference is given to using the R,S/R,R; S,S/S,R or S,R/R,R enantiomers in the process according to the invention for preparing 2-component mixtures, and the S,S/S,R/R,R; S,S/R,R/R,S or S,S/R,S/S,R enantiomers in the process according to the invention for preparing 3-component mixtures.

The insect- and mite-repellent action of the inventive compositions is long-lasting, as a synergistically active mixture. They can therefore be used with good success for repulsion of harmful or annoying, sucking and biting insects and mites.

The sucking insects include essentially the mosquitoes (e.g. *Aedes, Culex* and *Anopheles* species), sandflies (*Phlebotoma*), biting midges (*Culicoides* species), blackflies (*Simulium* species), biting houseflies (e.g. *Stomoxys calcitrans*), tsetse flies (*Glossina* species), horseflies (*Tabanus, Haematopota* and *Chrysops* species), common houseflies (e.g. *Muca domestica* and *Fannia canicularis*), fleshflies (e.g. *Sarcophaga carnaria*), flies which cause myiasis (e.g. *Lucilia couprina, Chrysomyia chloropyga, Hypoderma bovis, Hypoderma lineatum, Dermatobia hominis, Oestrus ovis, Gasterophilus intestinalis, Cochliomyia hominovorax*), bugs (e.g. *Cimex lectularius, Rhodnius prolixus, Triatoma infestans*), lice (e.g. *Pediculus humanus, Haematipinus suis, Damalina ovis*), louse flies (e.g. *Melaphagus orinus*), fleas (e.g. *Pulex irritans, Cthenocephalides canis, Xenopsylla cheopsis*) and sandfleas (e.g. *Dermatophilus penetrans*).

The biting insects include essentially cockroaches (e.g. *Blattela germanica, Periplaneta americana, Blatta orientalis, Supella supellectilium*), beetles (e.g. *Sitophilus granarius, Tenebrio molitor, Dermestes lardarius, Stegobium paniceum, Anobium punctactum, Hylotrupes bajulus*), termites (e.g. *Reticulitermes lucifugus*) and ants (e.g. *Lasius niger*).

The mites include ticks (e.g. *Ornithodorus Moubata, Ixodes ricinus, Boophilus microplus, Amblyomma hebreum*), and mites in the narrower sense (e.g. *Sarcoptes scabiei, Dermanyssus gallinae*).

The present invention thus also relates to the use of the inventive compositions described for insect and mite repulsion.

The invention further relates to formulations for insect and mite repulsion, which comprise the inventive compositions described, and optionally further active ingredients, carriers, solvents and/or dispersants, surfactants and further additives.

The inventive formulations may also comprise further insect repellents as well as the inventive compositions. Virtually all customary repellents are useful here.

In the case of repellent combinations, preference is given to using the inventive compositions described as a 2- or 3-component mixture together with repellent carboxamides, 1,3-alkanediols and carboxylic esters. The following should be mentioned specifically: N,N-diethyl-3-methylbenzamide (DEET), 2-ethylhexane-1,3-diol and diethyl phthalate.

The inventive formulations can be produced in all administration forms customary in cosmetics, for example in the form of solutions, emulsions, gels, ointments, pastes, creams, powders, sticks, sprays or aerosols from spray cans.

For use in the noncosmetic sector, the invention formulations can be used, for example, in the form of granules, oil sprays or slow-release formulations.

The invention further provides a process for producing formulations for insect and mite repulsion, in which the inventive compositions described are mixed with solvents and/or dispersants, carriers and/or surfactants, and optionally further active ingredients and/or additives.

The inventive formulations are preferably produced by mixing the inventive compositions with solvents (e.g. xylene, chlorobenzenes, paraffins, methanol, ethanol, isopropanol, water), carriers (e.g. polyoxyethylene fatty acid esters, polyoxyethylene fatty alcohol ethers, alkylsulphonates, arylsulphonates) and/or surfactants, and optionally additives.

The formulations contain generally between 0.1 and 95% by weight of the inventive compositions as a synergistically active 2- or 3-component mixture, preferably between 0.5 and 90% by weight, more preferably between 1 and 50% by weight, based on the overall formulation.

For protection against blood-sucking insects or mites, the inventive formulations are either applied to the human or animal skin, or items of clothing or other articles are treated therewith. The inventive formulations are also suitable as an addition of impregnating agent for, for example, textile sheets, items of clothing, packaging materials, and as an addition to polishes, cleaners and window cleaners.

EXAMPLES

Repulsion Tests

Repellent Effectiveness of Formulations for Use Against Mosquitoes on the Human Arm:

The insects, as an actively biting population (approx. 1000 mosquitoes of both genders), were kept in cages (length 90 cm, width 30 cm, height 40 cm, side walls made of gauze) which have 2 light fabric gates on the front side. The insects have been fed exclusively with sugared water (10% Dextropur). The age of the insects was at least 7 days; the number of insects was made up twice per week by three-day-old fully grown insects.

The biting activities were checked every hour continuously during the test period by exposing an untreated arm to the insects (an additional internal product standard was used by a selected volunteer).

The low electrical illumination of the cage was on from 6 am to 6 pm, with light from 6 pm to 6 am. The temperature was 25-27° C.; the relative air humidity was 50-70%.

The lower arms of the test subjects were washed with unperfumed soap, rinsed with water, then rinsed with a solution of 70% ethanol and 30% water, and dried with a towel.

90 cm² of each lower arm of a test subject was rubbed uniformly with 150 µl (or 150 mg) of the test product. As soon as the formulation was dry (after approx. 5 minutes), a sleeve with an opening of 3.1-8 cm (25 cm²) was tied around the arm such that the opening was completely over the treated surface. The corners of the opening of the sleeve had likewise been rubbed with the test material (200 µl) in a width of 1 cm in order to prevent bites at the corners. The area above the sleeve was protected with a towel through which the mosquitoes cannot penetrate. Hands were protected with latex gloves.

Both arms were introduced into the cage through the fabric gate, and the number of bites (and landings, if necessary) per arm was noted within a 3-minute test period. The test was repeated every hour up to 8 times, or ended beforehand if the effect ceased (three or more bites within 3 minutes or during 2 successive test sequences).

Each test consisted of 5 test subjects.

Mixtures of 2 or 3 enantiomers of the amino alcohol of the structure (1) in an ethanol/water (1:1) formulation were used. The synthesis and isolation of the individual enantiomers of the structure (1) by optical resolution, and the elucidation of the absolute configuration of the amino alcohols, are described in EP-A-2086327.

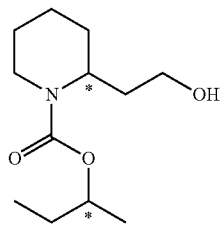

(1)

The results are compiled in Table A. The comparative standard used is the racemic mixture of all 4 enantiomers.

TABLE A

Repellent test against mosquitoes on the human lower arm

| Absolute configuration | Weight ratio | Increase in duration of action [%]* |
|---|---|---|
| S,S/1R,S | 1:1 | 9 |
| S,R/R,S | 1:1 | 8 |
| R,S/R,R | 1:1 | 21 |
| S,S/S,R | 1:1 | 15 |
| S,R/R,R | 1:1 | 18 |
| R,R/R,S/S,R | 1:1:1 | 10 |
| S,S/R,S/S,R | 1:1:1 | 13 |
| S,S/S,R/R,R | 1:1:1 | 28 |
| S,S/R,R/R,S | 1:1:1 | 25 |

The first descriptor in each case gives the absolute configuration in the sec-butoxycarbonyl unit, the second descriptor the absolute configuration in the 2-hydroxyethylpiperidine ring.
*Standard: Compared to the racemic mixture of all 4 enantiomers in a weight ratio of 1:1:1:1

What is claimed is:

1. An insect- and mite-repellent composition comprising at least 2 enantiomers selected from the group consisting of 1-[(S)-sec-butyloxycarbonyl]-2-(S)-(2-hydroxyethyl)piperidine (referred to hereinafter as S,S), 1-[(R)-sec-butyloxycarbonyl]-2-(R)-(+)-(2-hydroxyethyl)piperidine (referred to hereinafter as R,R), 1-[(S)-sec-butoxycarbonyl]-2-(R)-(+)-(2-hydroxyethyl)piperidine (referred to hereinafter as S,R), and 1-[(R)-sec-butyloxycarbonyl]-2-(S)-(+)-(2-hydroxyethyl)piperidine (referred to hereinafter as R,S), excluding the racemate mixture thereof.

2. The insect- and mite-repellent composition according to claim 1, wherein the composition comprises 2 of the enantiomers in a weight ratio of 1:1 or 3 of the enantiomers in a weight ratio of 1:1:1.

3. The insect- and mite-repellent composition according to claim 1, wherein the composition comprises the 2 enantiomers S,S/R,S; S,R/R,S; R,S/R,R; S,S/S,R or S,R/R,R.

4. The insect- and mite-repellent composition according to claim 1, wherein the composition comprises the 3 enantiomers R,R/R,S/S,R; S,S/R,S/S,R; S,S/S,R/R,R or S,S/R,R/R,S.

5. A process for preparing an insect- and mite-repellent composition according to claim 1 comprising mixing 2 enantiomers or 3 enantiomers from the group of the enantiomers S,S; R,R; S,R; and R,S, and wherein said mixing is optionally in the presence of a solvent.

6. A method of repelling insects and mites comprising applying the composition according to claim 1 to an area to be protected from insects and mites.

7. A formulation for insect and mite repulsion, comprising a composition according to claim 1 and optionally one or more further active ingredients, carriers, solvents and/or dispersants, surfactants or further additives.

8. The formulation according to claim 7, wherein the formulation comprises from 0.1 to 95% by weight, based on the overall weight of the formulation of the at least 2 enantiomers.

9. The formulation according to claim 7, wherein the formulation is in the administration form selected from the group consisting of a solution, an emulsion, a gel, an ointment, a paste, a cream, a powder, a stick, and a spray.

10. A process for producing a formulation for insect and mite repulsion according to claim 7, comprising mixing the at least 2 enantiomers with solvent and/or dispersant, carriers and/or surfactants, and optionally further active ingredients and/or additives.

* * * * *